US008524912B2

(12) United States Patent
Dembkowski et al.

(10) Patent No.: US 8,524,912 B2
(45) Date of Patent: Sep. 3, 2013

(54) PROCESS FOR THE PREPARATION OF [1-HYDROXY-2-(1H-IMIDAZOL-1-YL)-ETHYLIDENE]BISPHOSPHONIC ACID

(75) Inventors: Leszek Dembkowski, Pruszcz Gdanski (PL); Mariusz Krzyzanowski, Skórcz (PL); Robert Rynkiewicz, Starogard Gdanski (PL); Roman Szramka, Starogard Gdanski (PL); Zdzislaw Roznerski, Starogard Gdanski (PL); Daniel Zyla, Starogard Gdanski (PL); Janusz Rachon, Gdansk (PL); Slawomir Makowiec, Gdansk (PL)

(73) Assignee: Zaklady Farmaceutyczne Polpharma SA, Gdansk (PL)

( * ) Notice: Subject to any disclaimer, the term of this patent is extended or adjusted under 35 U.S.C. 154(b) by 216 days.

(21) Appl. No.: 13/126,636

(22) PCT Filed: Oct. 17, 2009

(86) PCT No.: PCT/PL2009/000092
§ 371 (c)(1),
(2), (4) Date: May 24, 2011

(87) PCT Pub. No.: WO2010/050830
PCT Pub. Date: May 6, 2010

(65) Prior Publication Data
US 2012/0116092 A1    May 10, 2012

(30) Foreign Application Priority Data
Oct. 31, 2008 (PL) .......................................... 386416

(51) Int. Cl.
*C07F 9/6506*    (2006.01)
(52) U.S. Cl.
USPC ....................................................... 548/112
(58) Field of Classification Search
USPC ....................................................... 548/112
See application file for complete search history.

(56) References Cited

U.S. PATENT DOCUMENTS
4,939,130 A    7/1990 Jaeggi et al.

FOREIGN PATENT DOCUMENTS

| EP | 0275821 A1 | 2/1992 |
|---|---|---|
| EP | 0275821 B1 | 2/1992 |
| WO | 03/093282 A1 | 11/2003 |
| WO | 03/097655 A1 | 11/2003 |
| WO | 2005/044831 A2 | 5/2005 |
| WO | 2005/063717 A1 | 7/2005 |
| WO | 2005/063779 A2 | 7/2005 |
| WO | 2005/066188 A1 | 7/2005 |
| WO | 2006/134603 A1 | 12/2006 |
| WO | 2007/069049 A2 | 6/2007 |
| WO | 2007/083240 A2 | 7/2007 |
| WO | 2007/096896 A1 | 8/2007 |
| WO | 2007/109542 A2 | 9/2007 |
| WO | 2008/035131 A1 | 3/2008 |
| WO | 2008/056129 A1 | 5/2008 |

OTHER PUBLICATIONS

Kabachnick et al., "Synthesis and Acid-Base and Complexing Properties of Amino-Substituted α-Hydroxyalkylidenediphosphonic Acids," Russian Chemical Bulletin, Institute of Heteroorganic Compounds, Academy of Sciences of the USSR, 1978, 374-377, vol. 27(2), translation of item No. 2, below)(the year of publication is sufficiently earlier than the effective U.S. filing date and any foreign priority date so that the particular month of publication is not in use) Plenum Publishing Corporation.

Kabachnick et al., "Synthesis and Acid-Base and Complexing Properties of Amino-Substituted α-Hydroxyalkylidenediphosphonic Acids," Izvestiya Akademii Nauk SSSR, Seriya Khimicheskaya, Feb. 1978, 433-437, vol. 2, (reason for disclosure—as set forth in specification, p. 1, lines 24-29; this provides method used by US4939130 for preparation of [1-hydroxy-2-(1H-imidazol-1-yl)-ethylidene]bisphosphonic acid).

International Search Report for International Application No. PCT/PL2009/000092, mailed Jan. 18, 2010, European Patent Office, Rijswijk, The Netherlands, 4 pages.

*Primary Examiner* — Joseph Kosack
(74) *Attorney, Agent, or Firm* — William D. Hare; McNeely, Hare & War LLP

(57) ABSTRACT

A process for the preparation of [1-hydroxy-2-(1H-imidazol-1-yl)-ethylidene]bisphosphonic acid consists of the reaction of aqueous solution of 1H-imidazole-1-acetic acid hydrochloride with phosphorus trichloride followed by removal of the excess of phosphorus trichloride, addition of water and hydrolysis of the reaction products. In order to isolate the product the post-reaction mixture is filtered and the anti-solvent is added to the aqueous filtrate in order to crystallize out [1-hydroxy-2-(1H-imidazol-1-yl)-ethylidene]bisphosphonic acid monohydrate.

5 Claims, No Drawings

PROCESS FOR THE PREPARATION OF [1-HYDROXY-2-(1H-IMIDAZOL-1-YL)-ETHYLIDENE]BISPHOSPHONIC ACID

CROSS-REFERENCE TO RELATED APPLICATIONS

This application is being filed under 35 USC 371 as a National Stage Application of pending International Application No. PCT/PL2009/000092 filed Oct. 17, 2009, which claims priority to parent Polish Patent Application No. P.386416 filed on Oct. 31, 2008 which are hereby incorporated by reference herein in their entirety for all they teach and disclose.

The invention relates to a novel process for the preparation of [1-hydroxy-2-(1H-imidazol-1-yl)-ethylidene]bisphosphonic acid.

[1-Hydroxy-2-(1H-imidazol-1-yl)-ethylidene]bisphosphonic acid is known under the INN name as zoledronic acid which is used in treatment of osteoporosis, Paget's disease of bone, cancer-induced hypercalcemia (elevated blood calcium level) and in cancer metastasis to bone. As zoledronic acid possesses affinity towards calcium, it is deposited in bones. Pharmacological action of zoledronic acid is based on stimulation of osteoblasts that results in creation of bone tissue and inhibition of calcification and osteoclast-dependent bone resorption. Known methods of preparation of [1-hydroxy-2-(1H-imidazol-1-yl)-ethylidene]bisphosphonic acid are based on the reaction of 1H-imidazole-1-acetic acid, phosphorus acid and phosphorus halide followed by treating the reaction mixture with water in order to perform hydrolysis to the final product. Phosphorus halide is selected from the group consisting of: phosphorus trichloride, phosphorus oxychloride, phosphorus pentachloride, phosphorus tribromide, phosphorus oxybromide and phosphorus pentabromide.

In the patent specification No. U.S. Pat. No. 4,939,130 the process of preparation of [1-hydroxy-2-(1H-imidazol-1-yl)-ethylidene]bisphosphonic acid in the reaction of 1H-imidazole-1-acetic acid hydrochloride with phosphoric acid and phosphorus trichloride in presence of chlorobenzene based on the method published by Kabachnick et al., Izvestiya Akademii Nauk SSR, Seriya Khimicheskaya, No. 2, pp. 433-437, February, 1978, was disclosed. In this process phosphorus acid is obtained in situ as a result of the reaction of phosphorus trichloride with aqueous solution of phosphoric acid, most often commercially available in form of 85% solution. The reaction occurs in the heterogenous system because of low solubilities in chlorobenzene, which makes mixing more difficult and limits the introduction into the commercial scale. Moreover, chlorobenzene is irritant and toxic for people and environment.

According to the patent application No. WO 2007/109542 use of diglyme as a solvent in the reaction of 1H-imidazole-1-acetic acid with phosphorus trichloride and phosphoric acid solves the problem of solidification of the reaction mixture. However, this increases the process costs and the disclosed process efficiencies are low, about 28%.

The most often used reaction of obtaining [1-hydroxy-2-(1H-imidazol-1-yl)-ethylidene]bisphosphonic acid is the reaction of 1H-imidazole-1-acetic acid with the phosphonating agent such as $H_3PO_3/PCl_3$ or $H_3PO_3/POCl_3$. Also for this reaction the number of publications implicates the problem of dense and heterogenic reaction mass which is solved by use of suitable solvents. According to the patent application No. WO 03/093282 ionic liquids that occur in liquid state in the temperature range precisely defined by their properties are used as the reaction medium. According to the patent application No. WO 03/097655 (PL373574A) reaction solvents like aromatic hydrocarbons with diatomaceous earth, silicone liquid or polyalkylene glycol with combination of phosphoric acid are proposed. However, the use of those solvents deteriorates the profitability of the process, makes isolation and purification of the product more difficult, which results in complication of process implementation into the industrial scale.

The preparation of [1-hydroxy-2-(1H-imidazol-1-yl)-ethylidene]bisphosphonic acid according to the patent application No. WO 2005/063779 discloses that the fluid reaction mass suitable for employment into the larger scale can be obtained by suitable selection of mole ratio of carboxylic acid, phosphorus acid and phosphorus oxychloride.

Unexpectedly, it was found that the use of phosphorus trichloride as a solvent and as a reagent in the reaction with 1H-imidazole-1-acetic acid hydrochloride in presence of water also leads to obtaining [1-hydroxy-2-(1H-imidazol-1-yl)-ethylidene]bisphosphonic acid, simultaneously ensuring the homogeneous reaction environment. Moreover, such solution allows for simplification of the process to a greater extent, which is advantageous for implementation into the industrial scale. Additionally, phosphorus trichloride is non-flammable, its boiling temperature favours heat removal from the reaction mixture and after treatment of the reaction mixture with water in the last stage only non-toxic phosphorus acid is generated.

The process of preparing [1-hydroxy-2-(1H-imidazol-1-yl)-ethylidene]bisphosphonic acid according to the invention consists of the following stages:
a) addition of aqueous solution of 1H-imidazole-1-acetic acid hydrochloride to phosphorus trichloride,
b) distilling off the excess of phosphorus trichloride,
c) treating the reaction mixture with water and conducting hydrolysis at the boiling temperature,
d) filtration of the post-reaction mixture,
e) treating the aqueous filtrate with anti-solvent to initialize the crystallization of [1-hydroxy-2-(1H-imidazol-1 -yl)-ethylidene]bisphosphonic acid,
f) isolation of zoledronic acid from the suspension.

The aqueous solution of 1H-imidazole-1-acetic acid hydrochloride is added to phosphorus trichloride at the temperature 0-5° C., then reaction is conducted at the temperature up to 85° C., preferably 80-85° C.

The term anti-solvent refers to the solvent in which a compound has a limited solubility.

In the method according to this invention this compound is [1-hydroxy-2-(1H-imidazol-1-yl)-ethylidene]bisphosphonic acid and methanol, ethanol, isopropanol or acetone are used as anti-solvents. [1-Hydroxy-2-(1H-imidazol-1-yl)-ethylidene]bisphosphonic acid is isolated in the form of crystalline monohydrate, most often of pharmaceutical quality. In case of necessity the quality of [1-hydroxy-2-(1H-imidazol-1-yl)-ethylidene]bisphosphonic acid may be improved by recrystallization in water/antisolvent system.

This invention is illustrated with the following examples that do not limit the invention in any way:

EXAMPLE I

Preparation of [1-hydroxy-2-(1H-imidazol-1-yl)-ethylidene]bisphosphonic acid A solution of 1H-imidazole-1-acetic acid [39 g (0.309 moles) of 1H-imidazole-1-acetic acid in 27 ml of water and 27 ml of hydrochloric acid (35-38%)] is added dropwise for 1-1.5 hour at the temperature 0-5° C. to 162 ml of phosphorus trichloride ($PCl_3$) cooled to the temperature 0-5° C. Then, the mixture is heated to 80-85° C. and maintained at this temperature for 2 hours. The excess of the phosphorus trichloride is then distilled off under the reduced pressure. 300 ml of water is added to the reaction residues and the hydrolysis is performed while maintaining boiling for 6 hours, afterwards 3.75 g of activated charcoal, 3.75 g of HYFLO SUPER CEL (diatomaceous earth) are added and mixed while boiling for 30 minutes. The mixture is filtered through 20 g of HYFLO SUPER CEL (diatomaceous earth) in a funnel. Charcoal with HYFLO SUPER CEL (diatomaceous earth) is washed with 30 ml of water. 300 ml of methanol is added for 1-1.5 hour to the filtrate at the temperature 55-60° C. The mixture is cooled to 20-25° C. After 5 hours of mixing at 20-25° C. the precipitate is filtered off, washed three times with 30 ml of water, once with 30 ml of methanol and dried for 6 hours at 55° C.

36.68 g (41%) of [1-hydroxy-2-(1$H$-imidazol-1-yl)-ethylidene]bisphosphonic acid monohydrate is obtained.

HPLC 99.98% , TGA 6.18%

12 g of [1-hydroxy-2-(1$H$-imidazol-1-yl)-ethylidene]bisphosphonic acid is suspended in 240 ml of water, heated to the boiling point and mixed while boiling for 15 minutes. Then the mixture is cooled to 60° C. and 240 ml of methanol is added for about 1 hour. The mixture is cooled to 20-25° C. After 3 hours of mixing in 20-25° C. the precipitate is filtered off, washed twice with 12 ml of water and once with 12 ml of methanol and dried for 6 hours at 55° C.

10.37 g (86%) of [1-hydroxy-2-(1$H$-imidazol-1-yl)-ethylidene]bisphosphonic acid monohydrate is obtained.

HPLC 100.00%, TGA 6.28%

XPRD: 12.04; 12.77; 15.69; 18.81; 20.83; 21.24; 21.69; 22.11; 25.71; 27.51; 29.18; 32.33; 32.89° (+,−0.02°) 2θ

$^1$H NMR (D$_2$O): δ=4.675-4.714 ppm (t, 2H, J=9.6); 7.379 (s, 1H); 7.547 (s, 1H); 8.717 (s, 1H)

$^{13}$C NMR: δ=55.65 ppm; 74.78-76.86 (t); 121.16; 126.76; 138.68

$^{31}$P NMR: δ=14.46 ppm

EXAMPLE II

Preparation of [1-hydroxy-2-(1$H$-imidazol-1-yl)-ethylidene]bisphosphonic acid

A solution of 1H-imidazole-1-acetic acid [26 g (0.206 moles) of 1H-imidazole-1-acetic acid in the mixture of 18 ml of water and 18 ml of hydrochloric acid (35%)] is added dropwise for 30 minutes at the temperature 0-5° C. to 108 ml of phosphorus trichloride (PCl$_3$) cooled to the temperature 0-5° C. The mixture is mixed at 0-5° C. for 1 hour. Then, the mixture is heated to 80° C. and maintained at this temperature for 1 hour. The excess of phosphorus trichloride is then distilled off under the reduced pressure. 200 ml of water is added to the reaction residues and the hydrolysis is performed while maintaining boiling for 6 hours, afterwards 1 g of activated charcoal, 5 g of HYFLO SUPER CEL (diatomaceous earth) are added and mixed while boiling for 30 minutes. The mixture is filtered and the filter is washed with 20 ml of water. The filtrate is concentrated under the reduced pressure to the volume of 100 ml. 150 ml of 95% ethanol is added to the concentrated filtrate at 70° C. The mixture is cooled while mixing to 25° C. and crystallization is performed until the temperature reaches 20-25° C. for 4 hours. The formed precipitate is filtered off, washed twice with 30 ml of water-ethanol mixture (1:1.5) and dried at 50° C.

29.3 g (49%) of [1-hydroxy-2-(1$H$-imidazol-1-yl)-ethylidene]bisphosphonic acid monohydrate is obtained.

HPLC 100.00% , TGA 6.30%

XPRD: 12.05; 12.77; 15.69; 18.80; 20.84; 21.25; 21.71; 22.09; 25.71; 27.50; 29.19; 32.42; 32.88° (+,−0.02°) 2θ

$^1$H NMR (D$_2$O): δ=4.670-4.709 ppm (t, 2H, J=9.65); 7.379 (s, 1H); 7.540 (s, 1H); 8.719 (s, 1H)

$^{13}$C NMR: δ32 55.56 ppm; 74.81-76.90 (t); 121.13; 126.83; 138.71

$^{31}$P NMR: δ=14.36 ppm 15 g of [1-hydroxy-2-(1$H$-imidazol-1-yl)-ethylidene]bisphosphonic acid is suspended in 300 ml of water, heated to the boiling point and mixed while boiling for 15 minutes. Then, the mixture is cooled to 70° C. and 300 ml of ethanol is added for about 1-1.5 hour. The mixture is cooled to 20-25° C. After 14 hours of mixing in 20-25° C. the precipitate is filtered off, washed twice with 15 ml of water and once with 15 ml of ethanol and dried for 6 hours at 55° C.

12.78 g (85%) of [1-hydroxy-2-(1$H$-imidazol-1-yl)-ethylidene]bisphosphonic acid monohydrate is obtained.

HPLC 100.00%, TGA 6.24%

XPRD: 12.05; 12.78; 15.72; 18.70; 20.82; 21.23; 21.70; 22.08; 25.70; 27.51; 29.14; 32.32; 32.88° (+,−0.02°) 2θ

$^1$H NMR (D$_2$O): δ=4.470-4.497 ppm (t, 2H, J=9.62); 7.164 (s, 1H); 7.367 (s, 1H); 8.421 (s, 1H)

$^{13}$C NMR: δ=53.00 ppm; 72.59 (t); 118.47; 123.66; 138.71

$^{31}$P NMR: δ=14.21 ppm

EXAMPLE III

Preparation of [1-hydroxy-2-(1$H$-imidazol-1-yl)-ethylidene]bisphosphonic acid

A solution of 1H-imidazole-1-acetic acid [13 g (0.103 moles) of 1H-imidazole-1-acetic acid in 9 ml of water and 9 ml of hydrochloric acid (35%)] is added for about 1 hour at the temperature 0-5° C. to 54 ml of phosphorus trichloride (PCl$_3$) cooled to the temperature 0-5° C. Then, the mixture is heated to 80-85° C. and maintained at this temperature for 2 hours. The excess of the phosphorus trichloride is then distilled off under the reduced pressure. 100 ml of water is added to the reaction residues and the hydrolysis is performed while maintaining boiling for 6 hours, the mixture is cooled to 85° C., afterwards 1.3 g of activated charcoal, 1.3 g of HYFLO SUPER CEL (diatomaceous earth) are added and mixed for 30 minutes at 80-85° C. The mixture is filtered and the precipitate on the filter is washed with 13 ml of water. 100 ml of isopropanol is added for 15 minutes to the filtrate at 65-55° C. The mixture is cooled to 25° C. After 18 hours of mixing at 20-25° C. the precipitate is filtered off, washed twice with 13 ml of water, once with 13 ml of water-isopropanol mixture (1:1) and once with 13 ml of isopropanol and dried for 5 hours at 50° C.

12.1 g (41%) of [1-hydroxy-2-(1$H$-imidazol-1-yl)-ethylidene]bisphosphonic acid monohydrate is obtained.

HPLC 100% , TGA 6.02% XPRD: 12.04; 12.76; 15.67; 18.79; 20.81; 21.23; 21.69; 22.11; 25.70; 27.48; 29.17; 32.36; 32.87° (+,−0.02°) 2 θ

$^1$H NMR (D$_2$O): δ=4.634-4.672 ppm (t, 2H, J=9.65); 7.330 (s, 1H); 7.538 (s, 1H); 8.639 (s, 1H)

$^{13}$C NMR: δ=55.84 ppm; 74.54-76.53 (t); 121.75; 126.50; 138.79

$^{31}$P NMR: δ=15.02 ppm 10 g of [1-hydroxy-2-(1$H$-imidazol-1-yl)-ethylidene]bisphosphonic acid is suspended in 200 ml of water, heated to the boiling point and mixed while boiling for 15 minutes. Then, the mixture is cooled to 70-75° C. and 200 ml of isopropanol is added for about 1-1.5 hour. The mixture is cooled to 20-25° C. After 3 hours of mixing at 20-25° C. the precipitate is filtered off, washed twice with 10 ml of water and once with 10 ml of isopropanol and dried for 5 hours at 55° C.

9.35 g (93.5%) of [1-hydroxy-2-(1H-imidazol-1-yl)-ethylidene]bisphosphonic acid monohydrate is obtained.

HPLC 100.00%, TGA 6.18%

XPRD: 12.02; 12.76; 15.67; 18.80; 20.80; 21.24; 21.68; 22.12; 25.71; 27.51; 29.16; 32.31; 32.89° (+,−0.02°) 2θ

$^1$H NMR (D$_2$O): δ=4.675-4.713 ppm (t, 2H, J=9.63); 7.381 (s, 1H); 7.542 (s, 1H); 8.719 (s, 1H)

$^{13}$C NMR: δ=55.59 ppm; 74.82-76.91 (t); 121.14; 126.83; 138.71

$^{31}$P NMR: δ=13.24 ppm

EXAMPLE IV

Preparation of [1-hydroxy-2-(1H-imidazol-1-yl)-ethylidene]bisphosphonic acid

A solution of 1H-imidazole-1-acetic acid [26 g (0.206 moles) of 1H-imidazole-1-acetic acid in 18 ml of water and 18 ml of hydrochloric acid (35%)] is added dropwise for 2 hours at the temperature 0-5° C. to 108 ml of phosphorus trichloride (PCl$_3$) cooled to the temperature 0-5° C. Then, the mixture is heated to 80-85° C. and maintained at this temperature for 1.5 hours. The excess of the phosphorus trichloride is then distilled off under the reduced pressure. 200 ml of water is added to the reaction residues and the hydrolysis is performed while maintaining boiling for 6 hours, afterwards 2.6 g of activated charcoal, 2.6 g of HYFLO SUPER CEL (diatomaceous earth) are added and mixed while boiling for 30 minutes. The mixture is filtered through the funnel with 10 g of HYFLO SUPER CEL (diatomaceous earth). The charcoal and HYFLO SUPER CEL (diatomaceous earth) are washed with 26 ml of water. 200 ml of acetone is added for 30 minutes to the filtrate at 55-45° C. The mixture is cooled to 25° C. After 4 hours of mixing at 20-25° C. the precipitate is filtered off, washed twice with 26 ml of water-acetone mixture (1:1) and dried for 5 hours at 55° C.

26.7 g (45%) of [1-hydroxy-2-(1H-imidazol-1-yl)-ethylidene]bisphosphonic acid monohydrate is obtained.

HPLC 99.91%, TGA 6.19%.

The invention claimed is:

1. A process for preparation of [1-hydroxy-2-(1H-imidazol-1yl)-ethylidene] bisphosphonic acid monohydrate in a reaction of 1H-imidazole-1-acetic acid with phosphorus trichloride, said process comprising:
   a) reacting an aqueous solution of 1H-imidazole-1-acetic acid hydrochloride with phosphorus trichloride, wherein the aqueous solution of 1H-imidazole-1-acetic acid hydrochloride is added to phosphorus trichloride,
   b) removing excess phosphorus trichloride,
   c) adding water and hydrolyzing reaction products,
   d) filtering post reaction mixture,
   e) adding anti-solvent to the filtrate,
   f) isolating [1-hydroxy-2-(1H-imidazol-1-yl)-ethylidene] bisphosphonic acid monohydrate from the suspension.

2. A process according to claim 1, wherein a temperature of addition of aqueous solution of 1H-imidazole-1-acetic acid hydrochloride to phosphorus trichloride is 0-5° C.

3. A process according to claim 1, wherein a temperature of the reaction of 1H-imidazole-1-acetic acid hydrochloride with phosphorus trichloride is 0-85° C.

4. A process according to claim 1, wherein the anti-solvent used for precipitation of [1-hydroxy-2-(1H-imidazol-1-yl)-ethylidene] bisphosphonic acid monohydrate is selected from the group consisting of methanol, ethanol, isopropanol, and acetone.

5. A process according to claim 1, wherein a temperature of the reaction of 1H-imidazole-1-acetic acid hydrochloride to phosphorus trichloride is 80-85° C.

* * * * *